United States Patent [19]

Kojima et al.

[11] 4,210,720

[45] Jul. 1, 1980

[54] PROCESS FOR FERMENTATIVELY PRODUCING VITAMIN $B_{12}$

[75] Inventors: Ichiro Kojima, Yokosuka; Hiroshi Sato, Kawasaki; Yasuo Fujiwara, Tokyo, all of Japan

[73] Assignee: Nippon Oil Company, Ltd., Tokyo, Japan

[21] Appl. No.: 908,630

[22] Filed: May 23, 1978

[30] Foreign Application Priority Data

May 26, 1977 [JP] Japan .................................. 52-60414

[51] Int. Cl.$^2$ .............................................. C12D 5/06
[52] U.S. Cl. ...................................... 435/42; 435/86; 435/830; 435/822
[58] Field of Search ............. 195/28 VB, 111; 435/86, 435/42

[56] References Cited

U.S. PATENT DOCUMENTS

| 2,785,068 | 3/1957 | Hanson et al. | 195/28 VB |
| 3,085,049 | 4/1963 | Rudy et al. | 195/28 VB |
| 4,119,492 | 10/1978 | Kojima | 195/28 VB |

FOREIGN PATENT DOCUMENTS 48-38880 11/1973 Japan.
49-15796 4/1974 Japan.
49-133596 12/1974 Japan.

OTHER PUBLICATIONS

Perlman, Advances in Applied Microbiology vol. 1, pp. 87–122, (1959).

*Primary Examiner*—Lionel M. Shapiro
*Attorney, Agent, or Firm*—Wenderoth, Lind & Ponack

[57] ABSTRACT

A process for fermentatively producing vitamin $B_{12}$, which comprises cultivating a vitamin $B_{12}$-producing microorganism belonging to at least one of the genus Arthrobacter and the genus Propionibacterium in the presence of a pre-cultivation product of a vitamin $B_{12}$-producing microorganism belonging to at least the other genus, and separating vitamin $B_{12}$ from the culture broth.

10 Claims, No Drawings

PROCESS FOR FERMENTATIVELY PRODUCING VITAMIN B$_{12}$

This invention relates to a process for fermentatively producing vitamin B$_{12}$ in an increased output, which comprises cultivating a vitamin B$_{12}$-producing microorganism belonging to at least one of the genus Arthrobacter and the genus Propionibacterium in the presence of a pre-cultivation product of a vitamin B$_{12}$-producing microorganism belonging to at least the other genus, and separating vitamin B$_{12}$ from the culture broth.

Vitamin B$_{12}$ participates in the in vivo metabolism of nucleic acids, fats, proteins, carbohydrates, etc. and is used widely as a prophylactic and therapeutic drug for anemia, neurotic diseases and hepatic troubles. There is much demand for it as pharmaceuticals for man, poultry and domestic animals, food additives and feed additives.

Nemerous suggestions have previously been made on the fermentative production of vitamin B$_{12}$. They include, for example, the extraction of vitamin B$_{12}$ from the fermentation broth obtained during the production of an antibiotic such as Streptomycin, and the separation of vitamin B$_{12}$ from the culture broth of a vitamin B$_{12}$-producing microorganism belonging to the genus Propionibacterium cultivated in a medium containing carbohydrates as a carbon source (D. Perlman, Advances in Applied Microbiology, Vol. 1, p. 87, Academic Press New York).

A method for producing vitamin B$_{12}$ by a fermentation technique has also been reported which involves the use of non-carbohydrate substances such as hydrocarbons, alcohols and ketones as a carbon source in place of natural carbohydrates which are disadvantageous in regard to cost and availability (Japanese Patent Publication No. 38880/73 and Japanese Laid-Open Patent Publication No. 133596/74.). These prior methods, however, have not come into commercial acceptance because the amount of vitamin B$_{12}$ in the resulting culture broth is small.

The method which can utilize non-carbohydrate materials as carbon sources has some advantage in that these carbon sources are available at low cost and in stable amounts of supply as the products of the petroleum industry and the petrochemical industry. In particular, alcohols and ketones are promising materials for fermentation media because of their good water miscibility.

A method is also known which comprises cultivating a vitamin B$_{12}$-producing hydrocarbon-assimilable microorganism of the genus Corynebacterium in combination with a vitamin B$_{12}$-producing hydrocarbon-assimilable micro-organism of the genus Rhodepseudomonas, and recovering vitamin B$_{12}$ in improved yields from the culture broth (Japanese Patent Publication No. 15796/74).

The present inventors have made investigations about the production of vitamin B$_{12}$ by the fermentation technique. As a result, they have surprisingly found that by cultivating a vitamin B$_{12}$-producing microorganism belonging to at least one genus of known vitamin B$_{12}$-producing microorganisms of the genus Propionibacterium which differs from the genus to which the vitamin B$_{12}$-producing microorganisms used in the aforesaid mixed cultivation belong, and vitamin B$_{12}$-producing microorganisms of the genus Arthrobacter which include the novel strains disclosed in the prior application of the present inventors (German OLS No. 2,704,070 corresponding to U.S. Ser. No. 763,539, now U.S. Pat. No. 4,119,492, issued Oct. 10, 1978) in the presence of a pre-cultivation product of a microorganism belonging to at least the other genus, the output of vitamin B$_{12}$ increases remarkably as compared with the case of cultivating vitamin B$_{12}$-producing micro-organisms of the different genera separately. For example, as shown in Examples and Comparisons to be given hereinbelow, the output of vitamin B$_{12}$ attained by the present invention is about 5 times as large as that attained by the separate cultivation of a vitamin B$_{12}$-producing microorganism of each genus.

It has also been found that the output of vitamin B$_{12}$ increases not only when a vitamin B$_{12}$-producing micro-organism of the genus Arthrobacter and a vitamin B$_{12}$-producing microorganism of the genus Propionibacterium are inoculated and cultivated in a culture medium either simultaneously or at different times (usually after pre-cultivating them; in the present application, such a grown microbial cell product is also termed a pre-cultivation product), or when they are separately cultivated in culture media for certain periods of time and then the living pre-cultivation products (containing the living vitamin B$_{12}$-producing micro-organisms) are mixed and cultivated optionally after supplying additional ingredients for the medium and/or microorganism strains, but also when a cultivation product of one of the B$_{12}$-producing microorganism is sterilized or the living cells are removed from it. Then the other B$_{12}$-producing microorganism and/or a living pre-cultivation product of the other is added.

Vitamin B$_{12}$-producing microorganisms belonging to the genus Arthrobacter can utilize not only non-carbohydrate substances but also carbohydrates such as glucose, sucrose, starch and molasses, and restrictions and disadvantages in regard to the ingredients of the culture medium can be removed.

It is an object of this invention therefore to provide a process for producing vitamin B$_{12}$ by fermentation with commercial advantage.

Other objects and advantages of this invention will become more apparent from the following description.

Examples of the vitamin B$_{12}$-producing micro-organisms of the genus Propionibacterium used in this invention are Propionibacterium shermanii (ATCC 8262, 9614, 9615, 9616, 9617, 13673; IFO 12391, 12426; IFO stands for Institute for Fermentation, Osaka, Japan), and Propionibacterium freudenreichii (ATCC 6207; IFO 12424).

Examples of the vitamin B$_{12}$-producing micro-organisms belonging to the genus Arthrobacter are Arthrobacter simplex (ATCC 6946, 13260, 15799; IFO 12069), Arthrobacter tumescens (ATCC 6947; IFO 12960), and Arthrobacter hyalinus (FERM-P No. 3125, ATCC 31263, DSM 867).

Arthrobacter hyalinus possesses the following microbiological properties which are not found in the description of "Bergey's Manual of Determinative Bacteriology", 7th edition. Accordingly, it was identified as a novel strain belonging to the genus Arthrobacter, and so named.

Microbiological properties of Arthrobacter hyalinus

1. Morphological properties
   Morphology: in the early stage of cultivation, long curved rods having a size of 0.8×4–5 microns, and some of them V-form; in the later stage of cultivation, changed to short rods with a size of 1.2×1.5 microns.
Motility: none
Gram staining: positive or negative
Formation of spores: none
2. Properties in cultivaton
  Nutrient agar plate culture: peripheral edge erose, umbonate, transparent, moistly shining
  Nutrient agar slant culture: growth poor, filiform, transparent, moistly shining
  Nutrient liquid culture: turbid
3. Physiological properties
  Growth temperature: 25°–35° C.
  Growth pH: 6–9
  Oxygen demand: facultatively anaerobic
  Liquefaction of gelation: none
  Litmus milk: slightly turned alkaline, and very slowly peptonized
  Indole: not generated
  Hydrogen sulfide: generated
  Reduction of nitrates: none
  Catalase: not formed
  Urease: formed
  Acid fastness: negative
  Decomposition of starch: none
  Fermentability of sugars: Neither acids nor gases are generated from glycerin, arabinose, xylose, fructose, galactose, glucose, mannitol, sorbitol, lactose, maltose, sucrose and raffinose.
  Asparagine: not decomposed
  Citric acid: not decomposed According to this invention, a vitamin $B_{12}$-producing microorganism belonging to at least one of the genus Arthrobacter and the genus Propionibacterium is cultivated in the presence of a pre-cultivation product of a vitamin $B_{12}$-producing microorganism belonging to at least the other genus, and vitamin $B_{12}$ is separated from the resulting culture broth.

The pre-cultivation product may be a pre-cultivation product obtained by inoculating and growing the vitamin $B_{12}$-producing strain in a culture medium, a living pre-cultivation product (containing living microbial cells), or a sterilized pre-cultivation product, or a pre-cultivation product from which living microbial cells have been removed.

The cultivation in accordance with the process of this invention can be performed in various modes. For example, pre-cultivation products obtained by cultivating a vitamin $B_{12}$-producing strain of the genus Arthrobacter (to be sometimes referred to simply as a strain of the genus Arthrobacter) and a vitamin $B_{12}$-producing strain of the genus Propionibacterium either separately or as a mixture are inoculated and cultivated in a culture medium either simultaneously or at different times. Or these strains are separately cultivated in culture media for certain periods of time, and then the living pre-cultivation products of both are mixed, or one cultivation product is mixed with the other which has been sterilized or from which the living microbial cells have been removed. The mixture is then cultivated in a culture medium after if desired supplying additional ingredients for the medium and/or a strain of a genus which differs at least from the strain which forms the above pre-cultivation product. Some specific embodiments of the cultivation process of this invention are shown below.

(i) An embodiment wherein a vitamin $B_{12}$-producing strain of the genus Arthrobacter and a vitamin $B_{12}$-producing strain of the genus Propionibacterium are pre-cultivated as a mixture or separately; then the mixed pre-cultivation product is inoculated in a culture medium; or the separate pre-cultivation products are inoculated in the culture medium either simultaneously or at different times; or the mixed pre-cultivation product and either one of the separate pre-cultivation products are inoculated in the culture medium either simultaneously or at different times.

(ii) An embodiment wherein a vitamin $B_{12}$-producing strain of the genus Arthrobacter and a vitamin $B_{12}$-producing strain of the genus Propionibacterium are mix-cultivated, and the resulting mixed pre-cultivation product is inoculated and cultivated in a culture medium.

(iii) An embodiment wherein a living pre-cultivation product of a vitamin $B_{12}$-producing strain of the genus Arthrobacter is mixed with a living pre-cultivation product of a vitamin $B_{12}$-producing strain of the genus Propionibacterium, and the mixture is cultivated with or without adding additional ingredients for the culture medium and/or a vitamin $B_{12}$-producing strain of at least one of the two genera described above.

(iv) An embodiment wherein a living pre-cultivation product of a vitamin $B_{12}$-producing strain of the genus Arthrobacter is mixed with a pre-cultivation product of a vitamin $B_{12}$-producing strain of the genus Propionibacterium which has been sterilized or from which the living microbial cells have been removed, and the mixture is cultivated with or without adding additional ingredients for the culture medium and/or a vitamin $B_{12}$-producing strain of the genus Arthrobacter.

(v) An embodiment wherein a vitamin $B_{12}$-producing strain of the genus Propionibacterium is inoculated in a living pre-cultivation product of a vitamin $B_{12}$-producing strain of the genus Arthrobacter and cultivated with or without adding additional ingredients for the culture medium.

(vi) An embodiment wherein a vitamin $B_{12}$-producing strain of the genus Propionibacterium is inoculated in a pre-cultivation product of a vitamin $B_{12}$-producing strain of the genus Arthrobacter which has been sterilized or from which the living microbial cells have been removed, and cultivated with or without adding additional ingredients for the culture medium.

(vii) An embodiment wherein a living pre-cultivation product of a vitamin $B_{12}$-producing micro-organism of the genus Propionibacterium is mixed with a pre-cultivation product of a vitamin $B_{12}$-producing strain of the genus Arthrobacter which has been sterilized or from which living microbial cells have been removed, and the mixture is cultivated with or without adding additional ingredients for the culture medium and/or a vitamin $B_{12}$-producing strain of the genus Propionibacterium.

(viii) An embodiment wherein a vitamin $B_{12}$-producing strain of the genus Arthrobacter is inoculated in a living pre-cultivation product of a vitamin $B_{12}$-producing strain of the genus Propionibacterium, and cultivated with or without adding additional ingredients for the culture medium.

(ix) An embodiment wherein a vitamin $B_{12}$-producing strain of the genus Arthrobacter is inoculated in a pre-cultivation product which has been sterilized or from which living microbial cells have been removed, and cultivated with or without adding additional ingredients for the culture medium.

In performing the process of this invention, the use of a liquid culture medium is preferred irrespective of whether a strain of the genus Propionibacterium and a strain of the genus Arthrobacter are cultivated separately or together. When a strain of the genus Propionibacterium alone is to be cultivated, standing cultivation is preferred. In the case of cultivating a strain of the genus Arthrobacter, cultivation is preferably carried out under aerobic conditions, and shaking cultivation or stirring cultivation is advantageous. When a mixture of living pre-cultivation products of strains of the two genera is to be cultivated, standing cultivation or cultivation under mild aerobic conditions is preferred. In the case of shaking cultivation, it is advantageous to use slow shaking conditions or to use an increased amount of the cultivation liquor. In the case of stirring cultivation under aeration, it is advantageous to adjust the aerobic conditions by decreasing the speed of aeration, or by decreasing the concentration of oxygen in the air, or by decreasing the stirring speed, or by a suitable combination of these procedures.

The composition of the culture medium can be varied as desired. For example, in the case of cultivating a strain of the genus Propionibacterium alone, useful carbon sources are, for example, carbohyrates such as glucose, sucrose, maltose, lactose, starch and molasses, organic acids such as lactic acid, and alcohols such as glycerol. Useful nitrogen sources are, for example, inorganic nitrogen compounds such as ammonium salts and nitrates, and organic nitrogen compounds such as peptone, yeast extract, casein, meat extract, corn steep liquor, urea, fermentation waste liquors, fish meal, and soybean residues. It is possible to add inorganic acid salts such as phosphates, magnesium salts, potassium salts, calcium salts, manganese salts, cobalt salts, iron salts, zinc salts, molybdenum salts and copper salts, and if desired, vitamins.

In the case of cultivating a strain of the genus Arthrobacter, suitable carbon sources include carbohydrates such as glucose, sucrose, maltose, lactose, starch and molasses; hydrocarbons such as n-paraffin and kerosene; alcohols such as methanol, ethanol, i-propyl alcohol, n-propyl alcohol, n-butyl alcohol, propylene glycol and glycerol; organic acids such as acetic acid, propionic acid, lactic acid, malic acid and succinic acid; esters such as ethyl acetate; and ketones such as acetone and methyl ethyl ketone. Nitrogen sources, inorganic salts and vitamins may be the same as those exemplified above with regard to the cultivation of the strain of the genus Propionibacterium alone.

When the strains of the two genera are mix-cultivated, carbon sources suitable for one or both of the genera may be used.

When the pre-cultivation products of strains of the two genera are used as a mixture, it is not particularly necessary to add additional ingredients for the culture medium. Carbon sources such as carbohydrates or alcohols may be added. Other ingredients of the culture medium may be added if that will result in an increased output of vitamin $B_{12}$.

In the case of cultivating a strain of the genus Propionibacterium, the cultivation temperature is about 25 to about 37° C., and the pH is about 3.0 to about 8.5. The suitable cultivation time is about 2 days to about 10 days. In the case of cultivating a strain of the genus Arthrobacter, the cultivation temperature is about 20° to about 40° C., and the pH of the culture medium is about 4.5 to about 9.5. The cultivation time is about 1 to 8 days. When the pre-cultivation products of strains of the two genera are mixed, the cultivation temperature is about 20° to about 40° C. and the pH is about 3.0 to about 9.5. The cultivation time is about 1 to about 10 days.

In this manner, vitamin $B_{12}$ can be produced in an increased yield by cultivating a vitamin $B_{12}$-producing strain of at least one of the genus Arthrobacter and the genus Propionibacterium in the presence of a pre-cultivation product of a vitamin $B_{12}$-producing strain of at least the other genus.

Vitamin $B_{12}$ formed in the culture broth can be recovered by conventional methods, for example by the method described in the prior application of the present inventors (German OLS No. 2,704,070 corresponding to U.S. Ser. No. 763,539). Since vitamin $B_{12}$ builds up mainly within the cultivated cells of the strains of the two genera, the culture broth is first centrifuged to obtain microbial cells. When it is desired to separate vitamin as cyano-type vitamin $B_{12}$ from the culture broth, a cyanogen ion is added to the microbial cells, and the pH is adjusted to 5 by an acid such as sulfuric acid, followed by boiling. When it is desired to separate vitamin $B_{12}$ as a coenzyme-type vitamin $B_{12}$ (5,6-dimethylbenzimidazole cobamide coenzyme), and as a hydroxyl-type vitamin $B_{12}$, the microbial cells are extracted in the dark with a solvent such as methanol, ethanol, acetone or pyridine.

The vitamin $B_{12}$ separated from the culture broth can be purified by extraction with phenol, adsorption by activated carbon, or column chromatography using an ion exchange resin or cellulose, or suitable combinations of these.

The following Examples further illustrate the present invention more specifically.

EXAMPLE 1

Propionibacterium shermanii (IFO 12426) was inoculated in a 500 ml Erlenmeyer flask containing 100 ml of a sterilized culture medium which contained, per liter of deionized pure water, 10 g of glucose, 10 g of sodium lactate, 30 g of Sun Growth (a power of the waste liquor of whiskey), 4.2 g of peptone, 4.2 g of yeast extract, 1.5 g of $Na_2HPO_4.12H_2O$, 1.5 g of $KH_2PO_4$, 0.5 g of $MgSO_4.7H_2O$, 10 mg of $FeSO_4.7H_2O$, 10 mg of $MnSO_4.4H_2O$, 10 mg of $ZnSO_4.7H_2O$, 5 mg of $Co(NO_3)_2$, 200 µg of $CuSO_4.5H_2O$, 10 µg of $MoO_3$, 10 g of $CaCO_3$, and 2 g of a powder of tomato juice, and cultivated for 5 days in a standing condition at 30° C. The concentration of vitamin $B_{12}$ formed at this time was 660 µg/l.

Separately, Arthrobacter hyalinus (FERM P-3125) was inoculated in a 500 ml Erlenmeyer flask containing 100 ml of a sterilized culture medium which contained, per liter of pure deionized water, 10 ml of isopropyl alcohol, 3 g of peptone, 1 g of yeast extract, 3 g of $NH_4NO_3$, 1.5 g of $Na_2HPO_4.12H_2O$, 0.4 g of $KH_2PO_4$, 0.5 g of $MgSO_4.7H_2O$, 10 mg of $FeSO_4.7H_2O$, 10 mg of $ZnSO_4.7H_2O$, 5 mg of $Co(NO_3)_2$, 200 µg of $CuSO_4.5H_2O$, 10 µg of $MoO_3$ and 5 g of $CaCO_3$, and cultivated under shaking at 30° C. for 2 days. The concentration of vitamin $B_{12}$ formed at this time was 151 µg/l.

In accordance with the process of this invention, 100 ml of Arthrobacter hyalinus was aseptically transferred to a 500 ml Erlenmeyer flask containing 100 ml of a pre-cultivation product of Propionibacterium shermanii. Glucose was added to a concentration of 20 g/l, and shaking cultivation was started. Four days after the starting of mixed cultivation, the concentration of vitamin $B_{12}$ formed was 3.8 mg/l (3800 µg/liter).

Isolation of vitamin B$_{12}$ from the culture broth was performed by the method shown below.

Two liters of the culture broth obtained by the same method as described above was centrifuged at a speed of 5,000 rpm for 10 minutes to separate microbial cells. The cells were suspended in 200 ml of a 1/10 N acetic acid buffer having a pH of 5.0, and 50 of a solution of potassium cyanide having a concentration of 1000 ppm was added. The mixture was maintained at 100° C. for 15 minutes. After cooling, the suspension of the microbial cells was centrifuged at a speed of 5,000 rpm for 10 minutes to remove the microbial cells. Then, 80% phenol (1/5 volume) was added, and the mixture was shaken. After standing, the phenol layer was collected and washed with water. Then, 1/5 part by volume of an equivolume mixture of water and ethyl ether was added, and the mixture was shaken. After standing, the aqueous layer was collected. The resulting aqueous solution of cyanocobalamine was purified by chromatography through ion-exchange cellulose, and finally recrystallized from acetone to afford 4.1 mg of cyanocobalamine.

For comparison, *Propionibacterium shermanii* was used alone, and cultivated at 30° C. in a standing state. On the fifth day, 100 ml of the aforesaid culture medium for the genus Arthrobacter was added and glucose was added to a concentration of 20 g/l. The standing cultivation was continued for four days. The concentration of vitamin B$_{12}$ formed was 780 µg/l.

For comparison, *Arthrobacter hyalinus* alone was cultivated under shaking, and on the second day of cultivation, 100 ml of the aforesaid culture medium for the genus Propionibacterium was added, and glucose was also added to a concentration of 20 g/l. The shaking cultivation was continued for 4 days. The concentration of vitamin B$_{12}$ formed was 570 µg/liter.

EXAMPLE 2

The procedure of Example 1 was repeated except that 100 ml of the pre-cultivation product of *Arthrobacter hyalinus* was subjected to a steam sterilizer at 121° C. for 10 minutes prior to use. The concentration of vitamin B$_{12}$ formed was 3.1 mg/liter (3100 µg/liter).

EXAMPLE 3

The procedure of Example 1 was repeated except that *Propionibacterium freudenreichii* (IFO 12424) was used instead of the *Propionibacterium shermanii*. After cultivation under shaking for 4 days, the concentration of vitamin B$_{12}$ formed was 1.58 mg/liter (1580 µg/liter).

For comparison, *Propionibacterium freudenreichii* was cultivated in a standing condition. After cultivation for 5 days, the concentration of vitamin B$_{12}$ formed was 270 µg/liter. To the culture broth was added 100 ml of the sterilized culture medium for the genus Arthrobacter as described in Example 1, and glucose was added to a concentration of 20 g/liter. When the shaking cultivation was continued for 4 days, the concentration of vitamin B$_{12}$ formed was 250 µg/liter.

EXAMPLE 4

The procedure of Example 3 was repeated except that *Arthrobacter simplex* (ATCC 6946) was used instead of the *Arthrobacter hyalinus*, and 10 g of glucose was used as a carbon source of a culture medium for *Arthrobacter simplex* instead of 10 ml of isopropyl alcohol. After cultivation for 4 days, the concentration of vitamin B$_{12}$ formed was 1.07 mg/l (1070 µg/l).

For comparison, *Arthrobacter simplex* alone was cultivated under shaking. On the second day of cultivation, the concentration of vitamin B$_{12}$ formed was 158 µg/liter. To the culture broth was added 100 ml of the sterilized culture medium for the genus Propionibacterium, and glucose was added to a concentration of 20 g/liter. The shaking culture was performed for 4 days. The concentration of vitamin B$_{12}$ formed was 230 µg/liter.

EXAMPLE 5

The procedure of Example 4 was repeated except that *Propionibacterium shermanii* (IFO 12426) was used instead of the *Propionibacterium freudenreichii*. After cultivation under shaking for 4 days, the concentration of vitamin B$_{12}$ formed was 2.7 mg/liter (2700 µg/liter).

EXAMPLE 6

The procedure of Example 5 was repeated except that 10 ml of n-paraffin was used instead of 10 g of glucose as a carbon source of the culture medium for *Arthrobacter simplex* (ATCC 6946). After cultivation under shaking for 4 days, the concentration of vitamin B$_{12}$ formed was 2.2 mg/liter (220 µg/liter).

For comparison, *Arthrobacter simplex* was singly cultivated under shaking. On the second day of the cultivation, the concentration of vitamin B$_{12}$ formed was 130 µg/liter. To the culture broth was added 100 ml of the sterilized culture medium for the genus Propionibacterium, and glucose was added to a concentration of 20 g/liter. Cultivation under shaking was continued for 4 days. The concentration of vitamin B$_{12}$ formed was 310 µg/liter.

EXAMPLE 7

The procedure of Example 5 was repeated except that *Arthrobacter tumescens* (IFO 12960) was used instead of *Arthrobacter simplex* (ATCC 6946). After cultivation under shaking for 4 days, the concentration of vitamin B$_{12}$ formed was 1.64 mg/liter (1640 µg/liter).

When *Arthrobacter tumuscens* was singly cultivated under shaking using the sterilized culture medium for *Arthrobacter simplex* as described in Example 4, the concentration of vitamin B$_{12}$ formed on the second day of cultivation was 175 µg/liter. To the culture broth was added 100 ml of the sterilized culture medium for the genus Propionibacterium as described in Example 1, and glucose was added to a concentration of 20 g/liter. When cultivation under shaking was performed for 4 days, the concentration of vitamin B$_{12}$ formed was 410 µg/liter.

Determination of vitamin B$_{12}$ in the culture broth in the above Examples was performed as follows: Potassium cyanide was added to a diluted culture broth, and the pH of the mixture was adjusted to 5. Then, it was boiled for 15 minutes to convert vitamin B$_{12}$ to cyanocobalamine. Then, it was determined by a microorganism assay method using *Lactobacillus leichimannii* (ATCC 7830).

What is claimed is:

1. A process for fermentatively producing vitamin B$_{12}$, which comprises cultivating a vitamin B$_{12}$-producing microorganism belonging to at least one of the genus Arthrobacter and the genus Propionibacterium, in the presence of a precultivation product of a vitamin B$_{12}$-producing microorganism belonging to at least the other genus, wherein the cultivation is carried out under one of the following conditions:

(i) precultivating a vitamin $B_{12}$-producing strain of the genus Arthrobacter and a vitamin $B_{12}$-producing strain of the genus Propionibacterium as a mixture or separately; then inoculating the mixed precultivation product in a culture medium; or inoculating the separate precultivation products in the culture medium either simultaneously or at different times; or inoculating the mixed precultivation product and either one of the separate precultivation products in the culture medium either simultaneously or at different times;

(ii) mix-cultivating a vitamin $B_{12}$-producing strain of the genus Arthrobacter and a vitamin $B_{12}$-producing strain of the genus Propionibacterium, and inoculating the resulting mixed precultivation product and cultivating it in a culture medium;

(iii) mixing a living precultivation product of a vitamin $B_{12}$-producing strain of the genus Arthrobacter with a living precultivation product of a vitamin $B_{12}$-producing strain of the genus Propionibacterium, and cultivating the mixture with or without adding additional ingredients for the culture medium and/or a vitamin $B_{12}$-producing strain of at least one of the two above genera;

(iv) inoculating a vitamin $B_{12}$-producing strain of the genus Propionibacterium in a living precultivation product of a vitamin $B_{12}$-producing strain of the genus Arthrobacter and cultivating it with or without adding additional ingredients for the culture medium;

(v) inoculating a vitamin $B_{12}$-producing strain of the genus Propionibacterium in a precultivation product of a vitamin $B_{12}$-producing strain of the genus Arthrobacter which has been sterilized or from which the living microbial cells have been removed, and cultivating it with or without adding additional ingredients for the culture medium;

(vi) mixing a living precultivation product of a vitamin $B_{12}$-producing microorganism of the genus Propionibacterium with a precultivation product of a vitamin $B_{12}$-producing strain of the genus Arthrobacter which has been sterilized or from which living microbial cells have been removed, and cultivating the mixture with or without adding additional ingredients for the culture medium and/or a vitamin $B_{12}$-producing strain of the genus Propionibacterium; or (vii) inoculating a vitamin $B_{12}$-producing strain of the genus Arthrobacter in a living precultivation product of a vitamin $B_{12}$-producing strain of the genus Propionibacterium, and cultivating it with or without adding additional ingredients for the culture medium;

to thereby produce a vitamin $B_{12}$-containing culture broth and then recovering vitamin $B_{12}$ from said broth.

2. The process of claim 1 wherein the cultivation is performed by precultivating a vitamin $B_{12}$-producing strain of the genus Arthrobacter and a vitamin $B_{12}$-producing strain of the genus Propionibacterium as a mixture or separately; then inoculating the mixed precultivation product in a culture medium; or inoculating the separate precultivation products in the culture medium either simultaneously or at different times; or inoculating the mixed precultivation product and either one of the separate precultivation products in the culture medium either simultaneously or at different times.

3. The process of claim 1 wherein the cultivation is performed by mix-cultivating a vitamin $B_{12}$-producing strain of the genus Arthrobacter and a vitamin $B_{12}$-producing strain of the genus Propionibacterium, and inoculating the resulting mixed precultivation product and cultivating it in a culture medium.

4. The process of claim 1 wherein the cultivation is performed by mixing a living precultivation product of a vitamin $B_{12}$-producing strain of the genus Arthrobacter with a living precultivation product of a vitamin $B_{12}$-producing strain of the genus Propionibacterium, and cultivating the mixture with or without adding additional ingredients for the culture medium and/or a vitamin $B_{12}$-producing strain of at least one of the two above genera.

5. The process of claim 1 wherein the cultivation is performed by inoculating a vitamin $B_{12}$-producing strain of the genus Propionibacterium in a living precultivation product of a vitamin $B_{12}$-producing strain of the genus Arthrobacter and cultivating it with or without adding additional ingredients for the culture medium.

6. The process of claim 1 wherein the cultivation is performed by inoculating a vitamin $B_{12}$-producing strain of the genus Propionibacterium in a precultivation product of a vitamin $B_{12}$-producing strain of the genus Arthrobacter which has been sterilized or from which the living microbial cells have been removed, and cultivating it with or without adding additional ingredients for the culture medium.

7. The process of claim 1 wherein the cultivation is performed by mixing a living precultivation product of a vitamin $B_{12}$-producing microorganism of the genus Propionibacterium with a precultivation product of a vitamin $B_{12}$-producing strain of the genus Arthrobacter which has been sterilized or from which living microbial cells have been removed, and cultivating the mixture with or without adding additional ingredients for the culture medium and/or a vitamin $B_{12}$-producing strain of the genus Propionibacterium.

8. The process of claim 1 wherein the cultivation is performed by inoculating a vitamin $B_{12}$-producing strain of the genus Arthrobacter in a living precultivation product of a vitamin $B_{12}$-producing strain of the genus Propionibacterium, and cultivating it with or without adding additional ingredients for the culture medium.

9. The process of claim 1 wherein the vitamin $B_{12}$-producing microorganism belonging to the genus Arthrobacter is a strain selected from *Arthrobacter simplex, Arthrobacter tumescens* and *Arthrobacter hyalinus.*

10. The process of claim 1 wherein the vitamin $B_{12}$-producing microorganism belonging to the genus Propionibacterium is a strain selected from the group consisting of *Propionibacterium shermanii,* and *Propionibacterium freudenreichii.*

* * * * *